United States Patent [19]
Illum

[11] Patent Number: 5,554,388
[45] Date of Patent: Sep. 10, 1996

[54] SYSTEMIC DRUG DELIVERY COMPOSITIONS COMPRISING A POLYCATIONI SUBSTANCE

[75] Inventor: Lisbeth Illum, Nottingham, United Kingdom

[73] Assignee: Danbiosyst UK Limited, Nottingham, United Kingdom

[21] Appl. No.: 167,611

[22] Filed: Dec. 14, 1993

Related U.S. Application Data

[63] Continuation of Ser. No. 743,328, filed as PCT/GB90/00291 published as WO90/09780, abandoned.

[30] Foreign Application Priority Data

Feb. 25, 1989 [GB] United Kingdom .................. 8904370

[51] Int. Cl.$^6$ .............................. A61K 9/50; A61K 9/14; A61K 9/20; A61K 47/36
[52] U.S. Cl. .................... 424/501; 424/426; 424/428; 424/430; 424/434; 424/435; 424/436; 424/437; 424/464; 424/469; 424/499; 514/772.3; 514/777; 514/778
[58] Field of Search .................... 424/423, 424, 424/425, 426, 427, 428, 430, 434, 435, 436, 437, 464, 468, 469, 484, 488, 489, 490, 493, 451, 499, 501; 514/2, 3, 772.3, 777, 778, 937, 960, 967; 530/303

[56] References Cited

U.S. PATENT DOCUMENTS

| | | | |
|---|---|---|---|
| 4,226,848 | 10/1980 | Nagai et al. | 514/772.1 |
| 4,946,870 | 8/1990 | Partain, III et al. | 514/777 |

FOREIGN PATENT DOCUMENTS

| | | |
|---|---|---|
| 0023359 | 2/1981 | European Pat. Off. . |
| 0122023 | 10/1984 | European Pat. Off. . |
| 0230264 | 7/1987 | European Pat. Off. . |
| 0312052 | 4/1989 | European Pat. Off. . |
| 3200766 | 9/1982 | Germany . |
| 2092002 | 11/1992 | United Kingdom . |
| 8809163 | 12/1988 | WIPO . |
| 8903207 | 4/1989 | WIPO . |

OTHER PUBLICATIONS

Biol. Abs. 75074688 (Sawayanagi et al., 1982, *Chem. & Pharm. Bull.*, "Directly Compressed Tablets containing Chitin or Chitosan in Addition to Mannitol", vol. 30 (11) pp. 4216–4218).

Chem. Abs. 112:84024c, vol. 112, 1990, (Manosroi et al., *Drug Dev. Ind. Pharm.*, 15 (14–16), 2531–2546, "The Entrapment of a Human Insulin–DEAE Dextran Complex in Different Compound Liposomes", (1989)).

Davis et al., Delivery Systems for Peptide Drugs, Plenum Press, New York, (1987).

Sawayanagi et al., Chem. Pharm. Bull., 31, 2062–2068 (1983).

Society for Experimental Biology, 24–29, Jul. 1988 "Mucas and Related Topics:".

T. Igawa et al., *Chem. Pharm Bull*, vol. 36, No. 8 pp. 3055–3059 (1988) "Enzyme Immunoassay of Human Fibroblast Interferon after Intranasal Administration with Several Excipients in Rabbits".

Y. Maitani, et al., "Influence of molecular weight and charge on nasal absorption of dextran and DAEA–dextran in rabbits", *Int. J. Pharm.*, vol. 49, pp. 23–27 (1989).

Davis, et al., Delivery Systems for Peptide Drugs, Plenum Press, New York, (1987).

Sawayanagi et al., "Dissolution Properties and Bioavailability of Phenytoin from Ground Mixtures with Chitin or Chitosan", *Chem. Pharm. Bull* vol. 31 pp. 2062–2068, (1983).

Anderson, M. T., et al., oral presentation at a meeting of the Society for Experimental Biology, Jul. 24–29, 1988, Manchester, U.K. "Mucas and Related Topics".

*Primary Examiner*—Carlos A. Azpuru
*Attorney, Agent, or Firm*—Arnall Golden & Gregory

[57] ABSTRACT

A composition for administration to the mucosa comprises a pharmacologically active compound and a polycationic substance. The polycationic substance is preferably DEAE-dextran or chitosan and the pharmacologically active compound is preferably insulin or calcitonin. The composition may be a solution, dispersion, powder or microspheres. Other enhancers, such as lysophosphatidylcholine, can be included if desired.

20 Claims, No Drawings

SYSTEMIC DRUG DELIVERY COMPOSITIONS COMPRISING A POLYCATIONI SUBSTANCE

This is a continuation of application Ser. No. 07/743,328 filed on Aug., 20 1990, now abandoned, and International Application PCT/GB90/00291 filed on Feb. 23, 1990.

The present invention relates to drug delivery compositions and more particularly to compositions which provide for the uptake of active drug material across mucosal surfaces, such as the vagina, colon or the nasal cavity.

A major problem in drug delivery is the effective absorption of high molecular weight material such as proteins and peptides across biological membranes. Normally such molecules are not taken up by the body if administered to the gastrointestinal tract, the buccal mucosa, the rectal mucosa, the vaginal mucosa or the intranasal mucosa. Recent studies with insulin have demonstrated that the absorption of such a compound can be increased if it is given together with a so-called absorption enhancer. These absorption enhancing materials have included surfactants of the non-ionic type as well as various bile salt derivatives. An increased permeability of membranes in the presence of these types of surfactant materials is obtained and the literature in the field of gastroenterology contains a wide range of such absorption promoters. (For a review see Davis et al (editors), Delivery Systems for Peptide Drugs, Plenum Press, New York, 1987) However, such materials will probably not be acceptable for the chronic administration of pharmacological agents because of their irritant effects on membranes. This includes not only the non-ionic variety of surface active agents but also bile salts and bile salt derivatives (e.g. fusidic acid).

EP-A-023 359 and EP-A-122 023 describe a powdery pharmaceutical composition for application to the nasal mucosa and methods for administration thereof. The pharmaceutical composition allows polypeptides and derivatives thereof to be effectively absorbed through the nasal mucosa. Similarly, U.S. Pat. No. 4,226,848 describes a method for administering a powdery medicament to the nasal mucosa where the preferred composition has mucoadhesive properties.

EP-A-230 264 describes an aqueous nasal drug delivery system for vaccines containing a high molecular weight drug, a gelling agent (e.g. hydroxyethylcellulose) and in some cases other additives (e.g. surfactants, glycerol and polyethyleneglycol) but, again, the composition is administered as a powder.

Microsphere-containing formulations have been described in WO 88/09163. The formulations contain certain enhancers to aid effective penetration of the mucosa by the drug. Our co-pending application WO 89/03207 further describes formulations which do not require an enhancer. These formulations may comprise drug-containing microcapsules which are coated with DEAE-dextran.

DEAE-dextran has been proposed for use in oral drug delivery formulations, where it is believed to interact with gastrointestinal mucins (Anderson, M. T. et al, oral presentation at a meeting of the Society for Experimental Biology, 24–29 July 1988, Manchester, U.K.) and has been delivered to the nasal cavities of rabbits as a model compound to study the absorption of peptides of differing sizes (Maitani, Y., et al, Int. J. Pharm. 1989, 49, 23–27).

Igawa et al (1988 Chem. Pharm. Bull. 36(8) 3055–3059) administered human interferon-β intranasally to rabbits with a DEAE-dextran excipient. The dextran part of the latter had an average molecular weight of 9000 and did not enhance the absorption of the drug, and the authors concluded that low MW excipients were to be preferred to high MW components. In view of this, it is surprising to find, as we now have, that a solution or dispersion of relatively high MW DEAE-dextran or other polycationic substances such as chitosan can form the basis of an improved formulation which does not require other enhancers, although the presence of other enhancers may further improve the performance of the compositions.

GB-A-2 092 002 discloses magnesium- and calcium-chelating compounds for enhancing the absorption of drugs through a digestive organ. Such compounds included polyamino acids. Sawanagi et al (1982) Chem. Pharm. Bull. 30(11), 4216–4218) disclosed the use of chitosan to bind the ingredients of tablets for retention in the mouth. Delivery to non-oral mucosal surfaces was not disclosed.

One aspect of the invention provides a composition for administration to mucosa comprising a pharmacologically active compound and a polymeric substance having a plurality of cationic groups (hereinafter "a polycationic substance" characterised in that (i) the substance is not a polyamino acid which chelates calcium or magnesium ions, (ii) the composition does not consist of microcapsules coated with DEAE-dextran, (iii) if for administration to gut mucosa, the composition does not consist of the active compound and a solution of DEAE-dextran and (iv), if in the form of a tablet for retention in the mouth, the composition does not comprise chitosan.

The polycationic substance may be present as a solution in an aqueous medium, as a dispersion in an aqueous system, as a powder or as microspheres. Preferably, such microspheres are formed from the polycationic substance itself (usually with the pharmacologically active substance incorporated as well) with or without other suitable microsphere-forming substances such as (human) serum albumin and derivatives and analogues thereof.

Preferably, the concentration of the polycationic substance in such a solution is 0.01 to 50% w/v, more preferably 0.1 to 50%, more preferably 0.2% to 30% and most preferably 0.5–15%. Diethylaminoethyl-dextran (DEAE-dextran) is a polycationic derivative of dextran containing diethylaminoethyl groups coupled to the glucose residues by ether linkages. The parent dextran can have an average molecular weight of about 5,000 to $40 \times 10^6$ but is typically about 500,000. In the context of the present invention, the term is limited to dextran of MW 10000 or more. The nitrogen content is usually approximately 3.2% which corresponds to one charged group to three glucose units. "Tandem" groups, which are introduced as the result of side reactions, result in the presence of three different basic groups in approximately equal ratios.

Chitosan is deacetylated chitin, or poly-N-acetyl-D-glucosamine. It is available from Protan Laboratories Inc, Redmond, Wash. 98052, USA and, depending on the grade selected, can be soluble in water up to pH 6.0. A 1% solution of non-water soluble chitosan (Sea Cure) may be made by making a slurry (eg 2 g/100 ml) in water and adding an equal volume of organic acid (eg 100 ml of 2% acetic acid) and stirring vigorously for one hour. Water-soluble chitosan (Sea Cure+) may dissolve without organic or inorganic acids being present.

Chitosan has previously been used to precipitate proteinaceous material, to make surgical sutures and as an immunostimulant. It has also been employed previously in oral drug formulations in order to improve the dissolution of poorly soluble drugs (Sawayanagi et al, Chem. Pharm. Bull., 31, 2062–2068 (1983)) or for the sustained release of drugs (Nagai et al, Proc. Jt. US-Jpn. Semin. Adv. Chitin, Chitosan, Relat. Enzymes, 21–39. Zikakis J. P. (ed), Academic Press.

Orlando (1984)) by a process of slow erosion from a hydrated compressed matrix.

DEAE-dextran and chitosan are preferred, but further polycationic substances which may be used in the compositions of the invention include other polycationic carbohydrates such as but not limited to inorganic or organic salts of chitosan and modified forms of chitosan (especially more positively charged ones), polyaminoacids such as polylysine, polyquaternary compounds, protamine, polyimine, DEAE-imine, polyvinylpyridine, polythiodiethylaminomethylethylene (P(TDAE)), polyhistidine, DEAE-methacrylate, DEAE-acrylamide, poly-p-aminostyrene, polyoxethane, co-polymethacrylates (e.g. copolymers of HPMA, N-(2-hydroxypropyl)-methacrylamide), GAFQUAT (U.S. Pat. No. 3,910,862) and polyamidoamines. The polycationic substances used in the invention have a molecular weight of 10,000 or more, preferably at least 100,000 or 200,000 and most preferably about 500,000. The chitosan (or a salt thereof) preferably has an intrinsic viscosity of at least 400 ml/g, more preferably at least 500, 750 or 1000 ml/g.

If desired, other enhancers may be included in the compositions of the invention, for example lysophosphatidylcholine and generally all those mentioned in WO 88/09163. Gelling agents or viscosity-increasing substances may be added in order to help retain the formulation on the mucosa. The chitosan, in particular, may be formulated as microspheres with or without albumin.

The compositions may be prepared at a neutral pH, i.e. pH 6.5–7.5, preferably about 7.3, for example using a standard phosphate buffer or at lower pH, for example pH4, by addition of HCl to the above or by use of an alternative buffer system. However, it has been found that DEAE-dextran or chitosan in combination with at least some drugs, for example insulin and most if not all other proteins, form a complex. At lower or higher pH's, i.e. away from the isoelectric point of the polycation and the drug, this complex may be present as a true solution instead of a dispersion. This may be advantageous, although it is also the case that very low pH's are more likely to irritate or even harm the mucosa. Thus, the man skilled in the art will be able to determine the optimal pH, which may lie between 1.0 and 11.0, preferably 4.0 to 7.5, for example 4.0 to 6.0, or 9.0 to 11.0.

The said complex may be isolated. The complex and its therapeutic utilities form further aspects of the invention.

The term "pharmacologically active compound" includes drugs, vaccines and components thereof (for example isolated antigens or parts thereof) and monoclonal antibodies.

The compositions may be used with drugs selected from the following non-exclusive list: insulin, calcitonins (for example porcine, human, salmon, chicken or eel) and synthetic modifications thereof, enkephalins, LHRH and analogues (Nafarelin, Buserelin, Zolidex), GHRH (growth hormone releasing hormone), nifedipin, THF(thymic humoral factor), CGRP (calcitonin gene related peptide), atrial natriuretic peptide, antibiotics, metoclopramide, ergotamine, Pizotizin, nasal vaccines (particularly AIDS vaccines, measles, rhinovirus Type 13 and respiratory syncitial virus), pentamidine and CCK (cholecystykinin).

Further drugs include: antibiotics and antimicrobial agents such as tetracycline hydrochloride, leucomycin, penicillin, penicillin derivatives, erythromycin, sulphathiazole and nitrofurazone; local anaesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitro-glycerine and papaverine hydrochloride; antiseptics such as chlorhexidine hydrochloride, hexylresorcinol, dequaliniumchloride and ethacridine; enzymes such as lysozyme chloride, dextranase; bone metabolism controlling agents such as vitamin D, and active vitamin $D_3$; sex hormones; hypotensives; sedatives; anti-tumor agents; steroidal anti-inflammatory agents such as hydro-cortisone, prednisone, fluticasone, prednisolone, triamcinolone, triamcinolone acetonide, dexamethasone, betamethasone, beclomethasone, and beclomethasone dipropionate; non-steroidal anti-inflammatory agents such as acetaminophen, aspirin, aminopyrine, phenylbutazone, mefanamic acid, ibuprofen, diclofenac sodium, indomethacin, colchicine, and probenocid; enzymatic anti-inflammatory agents such as chymotrypsin and bromelain seratiopeptidase; anti-histaminic agents such as diphenhydramine hydrochloride, chlorpheniramine maleate and clemastine; and anti-allergic agents and antitussive-expectorant antiasthmatic agents such as sodium chromoglycate, codeine phosphate, and isoproterenol hydrochloride.

The compositions can be administered via the nasal route using a nasal spray device, pressurized aerosol cannister or simple instillation means. The compositions may gel on the mucosa, at least to some extent, and this may facilitate retention of the composition on the mucosa. Formulations suitable for delivery of drugs to the colon can be subdivided into a number of technical categories known to those skilled in the art of pharmaceutical formulation. These can utilise coated solid dosage forms, such as tablets, pellets, mini-tablets, hard gelatin capsules etc or coated semi-solid preparations, such as soft gelatin capsules and the like. Enteric coated systems, based for example on methacrylate copolymers such as Eudragit L (Poly (methacrylic acid, methyl methacrylate)), are only soluble at pH 6 and above, so that the polymer only begins to dissolve on entry into the small intestine. The site of the disintegration is then dependent on the rate of intestinal transit and the amount of polymer present, a relatively thick polymer coating having been defined for delivery to the proximal colon (Hardy et al, Aliment. Pharmacol. Therap., 1, 273–280, (1987)). Polymers capable of providing site-specific colonic delivery can be utilised. These typically rely on the bacterial flora of the large bowel to provide enzymatic degradation of the polymer coat and hence release of the drug. A number of candidate materials appear promising, such as the azopolymers (Saffran et al, U.S. Pat. No. 4,663,308), glycosides (Friend et al, J. Med. Chem., 27, 261–266, (1984)) and a variety of naturally available and modified polysaccharides (Archer & Ring PCT Application GB89/00581).

Novel pulsed release technology (Magruder et al, U.S. Pat. No. 4,777,049) and the like, which permits drug delivery at a predetermined time, is now available. Such systems can be used to deliver both drug and polycationic substance, together with other additives that may alter the local microenvironment to promote drug stability and uptake, directly to the colon and do not rely on external conditions to provide in vivo release, except for the presence of water.

A further aspect of the invention provides a method of treating a human or other mammal by administering a composition as described above to a mucosal surface of that human or other mammal, for example the vagina, eye, colon or nasal cavity.

Embodiments of the present invention will now be described by way of example.

EXAMPLE 1

Insulin Plus DEAE-Dextran

A rat in vivo experimental model, modified from that originally described by Hirai et al (1981 Int. J. Pharm., 7

317–325) and Fisher et al (1987 J. Pharm. Pharmacol., 39 357–362), was used to study the intranasal absorption of insulin aqueous solutions. Male Wistar rats (Bantin and Kingman) of approximate weight 200–250 g, fasted overnight for about 20 hours, are anaesthetised by i.p. injection of 80 mg/kg pentobarbitone sodium (60 mg/ml Sagatal (Regd. T.M.) May and Baker) with further i.p. injections of 0.05 ml when necessary to maintain a suitable level of anaesthesia. The rats are tracheotomized, the oesophagus sealed and the carotid artery and jugular vein cannulated.

Insulin (semisynthetic human Na-insulin) solutions were prepared in $\frac{1}{15}$ M phosphate buffer of pH 7.3 to give a concentration of 167 IU/ml and the DEAE-dextran added to give concentrations of 10% w/v, 5% w/v or 1% w/v. The DEAE-dextran used in these experiments has a molecular weight of 500,000.

It is also possible to make up a solution of 334 IU/ml of insulin in phosphate buffer and add equal volumes of the DEAE-dextran in phosphate buffer of 20, 10 or 2% strength. This will give the same end solutions. When mixing the insulin solution with the DEAE-dextran the solution becomes turbid indicating that an interaction between the insulin and the DEAE-dextran has taken place.

An insulin solution containing the Laureth-9 enhancer system was prepared in a similar way.

The insulin solution alone or the insulin solutions containing the Laureth-9 or the various concentrations of DEAE-dextran were administered nasally to rats (n=4) at 16.7 IU/kg bodyweight using a Hamilton microsyringe. A volume of 20 μl was administered.

Blood samples of 0.2 ml were collected in Fluoride oxalate tubes from the carotid artery at 10 and 5 min. prior to the insulin administration and at 5, 15, 30, 45, 60, 90, 120, 180, 240 and 300 min. post-administration. The samples were kept for a short time on crushed ice until analysed on a Yellow Springs 23 AM glucose analyser by the glucose oxidase method.

Table 1 shows the approximate glucose levels (mmol/l) of rats given a dose of insulin in phosphate buffer and doses of insulin in phosphate buffer (pH 7.3) containing 1%, 5% or 10% DEAE-dextran measured at 120 minutes after administration. The level at the time of administration was about 3.5–4.0 mmol/l. The results show that insulin given intranasally as a simple phosphate buffer solution (pH 7.3) does not significantly lower the blood glucose level whereas the addition of the DEAE-dextran causes fast and significant decreases in blood glucose levels. The effect increases with increasing concentration of DEAE-dextran. The rats given the 10% concentration died early of hypoglycaemia. Administration of phosphate buffer alone shows a similar trend to that of the insulin solution alone, i.e. an increase in plasma glucose from about 3.5–4.0 mmol/l to about 5 mmol/l.

TABLE 1

|  | Blood glucose level (mmol/l) |
| --- | --- |
| Insulin plus DEAE-dextran 1% | 1.6 |
| Insulin plus DEAE-dextran 5% | 1.2 |
| Insulin plus DEAE-dextran 10% | 1.0 |
| Insulin alone | 5.1 |

For comparison, the glucose levels of rats given a dose of insulin in phosphate buffer and rats given a dose of insulin in phosphate buffer containing 0.5% Laureth-9 show that this well known effective enhancer system gives a decrease in blood glucose concentration similar to the 1% DEAE-dextran (about 1.9 mmol/l at 120 mins).

EXAMPLE 2

Effect of pH on Insulin/DEAE-Dextran Solutions

Solutions containing DEAE-Dextran 1% w/v and Na-Insulin 167 IU/ml were prepared, separately and combined, in phosphate buffer (pH 7.3) and their pH measured using a Gallenkamp pH Stick. The appearance of each solution was noted. The effect of addition of 1M sodium hydroxide solution (NaOH) or 0.1M hydrochloric acid (HCl) was determined. The two separate solutions were each clear (DEAE-D pH 6.58; Insulin pH 7.38) whereas the mixture (pH 6.65) was turbid.

The addition of 0.1M HCl to solutions of DEAE-dextran alone had no effect on solution appearance which remained clear. Solutions of Na-insulin however, became turbid when the pH reached 6.65 but cleared after further addition of acid lowered the pH to 4.14. Solutions of DEAE-dextran combined with Na-Insulin became less turbid after the addition of acid and were clear at pH 4.14. The addition of 1.0M NaOH to solutions of DEAE-dextran and Na-insulin alone had no effect on solution appearance which remained clear. Combined solutions of DEAE-dextran and Na-insulin however became less turbid as the pH increased and formed a clear solution when the pH reached 9.32. Solutions of DEAE-dextran and Na-insulin at about pH 4.0 were found to be at least as effective as those at about pH 6.6 in the rat model described above.

EXAMPLE 3

Toxicity of a Composition of the Invention

Insulin 100 IU/ml with DEAE-Dextran 5% w/v

The effects of the DEAE-dextran formulation on the nasal mucosa in rats (after 60 min incubation) were less dramatic than those of prior art surfactant enhancers. A few cells lost from the septum and turbinates were visible and mucus discharge on the dosed side resulted in a slight decrease in epithelium height. The clear cell structure was not so well defined and cytoplasmic space appeared reduced. The epithelium still appeared to be more than one cell thick (i.e. pseudostratified) and formed a continuous layer, though the arrangement of nuclei above the basement membrane was altered. Cilia were not always distinct amongst the discharged mucus.

Considerable amounts of AB staining mucus were still apparent in cells on the dosed side though there was generally not the confluent spread of filled goblet cells as on the undosed side. Some mucus was again present in the undosed cavity of some animals.

Effects of this formulation were generally restricted to the ventral half of the cavity and lateral nasoturbinate i.e. the dorsal meatus was unaffected.

EXAMPLE 4

(Comparative Example) Toxicity of Prior Art Composition

Insulin 100 IU/ml with STDHF 1% w/v

As compared to DEAE-dextran 5% w/v, STDHF (sodiumtaurodihydroxyfusidate) administered in the same way to rats and incubated for 60 mins showed obvious disruption to the nasal epithelium. Large volumes of mucus were apparent together with cell loss, epithelium rearrangement and considerable reduction of epithelium height to about half that on the undosed side. Generally the full length of the dosed septum and turbinates were affected. AB staining showed that some mucus remained in many of the epithelial cells but others had discharged their whole mucus content, particularly where the epithelium was reduced to a thin single cell layer such as in the middle meatus.

Some mucus was apparent on the undosed septum or drained into the dorsal meatus, but with no cell loss. The undosed turbinates were unaffected. Epithelial height on the dosed side was consistently less than that on the undosed 'control' side.

EXAMPLE 5

Insulin Plus Chitosan in the Rat

This Example was performed to evaluate the effect of chitosan, low or medium viscosity water soluble formulations (Sea cure$^+$), at different concentrations and at pH values of 4 and 7.3–7.4 on the intranasal absorption of insulin in rats (n=4).

Semisynthetic Na-insulin and chitosan (Sea cure$^+$) (water soluble powder) low viscosity (l.v.) and medium viscosity (m.v) from Protan Laboratories Inc. were used.

All insulin solutions were initially made in 14.65 mM phosphate buffer of pH 7.3–7.4 prepared from 1.904 g/l $Na_2HPO_4.2H_2O$ and 0.616 g/l $NaH_2PO_4.2H_2O$ in double distilled water. Adjustment of the pH to 4 where necessary was made by the addition of 150 µl of 0.1M HCl per ml of solution. Each 1 mg of insulin was considered equivalent to 28 IU. Double-strength insulin stock solutions were prepared freshly as follows: 159.9 IU/ml (6.74 mg/ml) for administration at pH 7.3–7.4 and 183.8 IU/ml (7.75 mg/ml) for administration at pH 4, accounting for the dilution by the addition of 0.1M HCl. The expected water content of the insulin is 15.3%.

Double strength chitosan solutions were prepared as follows: 0.2% w/v l.v. (2 mg/ml) for use at pH 7.3–7.4; 1.0% w/v l.v. (10 mg/ml) for use at pH 7.3–7.4; 0.2% w/v l.v. (2.3 mg/ml) for use at pH 4; 1.0% w/v l.v. (11.5 mg/ml) for use at pH 4; and 0.2% w/v m.v. (2.3 mg/ml) for use at pH 4.

Insulin/chitosan formulations were prepared by mixing equi-volumes of the appropriate stock insulin and chitosan solutions and the addition of 150 µl/ml of 0.1M HCl where necessary. Solutions were administered intranasally to rats at 100 µl/kg, corresponding to doses of 8 IU/kg insulin with 0.1 or 0.5 mg/kg l.v. chitosan or 0.1 mg/kg m.v. chitosan. A dose of 100 µl/kg of Insulin (167 IU/ml) is instilled into the nasal cavity via a microsyringe (Hamilton) and 0.61 mm o.d. polypropylene tubing (Portex).

Blood samples of 150 µl (8–12 drops) were collected from the carotid artery in fluoride oxalate blood tubes at 10, 6 and 2 minutes pre-administration and 5, 10, 15, 20, 40, 60, 90, 120, 180 and 240 minutes post-administration. Fluid replacement was given in the form of 0.9% saline via the jugular vein. The glucose levels of the samples were assayed within 2 hours of being taken using the glucose oxidase method on a Yellow Springs 23AM glucose analyser.

The pH 4 solutions were not buffered systems. A suitable buffered system may be devised if desirable.

All of the formulations gave a rapid fall in blood glucose levels, the 0.5% l.v. pH 4.0 solution reducing the level from 100% to about 16% after 60 minutes. Generally, 0.5% material was more effective than 0.1% and pH 4.0 was better than pH 7.3–7.4.

EXAMPLE 6

Insulin Plus Chitosan in the Sheep

Semi-synthetic human Na-insulin supplied by Nordisk, Gentofte was used. The water content of the sample was determined by spectrophotometry to be approximately 15%. Chitosan SEA CURE+, which is water soluble, of low (intrinsic viscosity 388 ml/g) and medium viscosity (intrinsic viscosity 1010 ml/g) were obtained from Protan Laboratories Inc. These will be referred to as CSN LV and CSN MV, respectively. Sixteen cross-bred sheep of known weight were used. The animals were not fasted prior to insulin administration. An in-dwelling Viggo secalon cannula of 1.2 mm i.d., fitted with a secalon universal flow-switch, was placed approx. 15 cm into one of the external jugular veins of each animal on the first day of the study and, whenever necessary, was kept patent by flushing it with heparinised normal saline (25 IU/ml). This cannula was removed upon the completion of the study.

An insulin solution of 19.32 mg/ml (460 IU/ml) was prepared in 14.65 mM phosphate buffer (0.476 g $Na_2HPO_4.2H_2O$+0.154 g $Na_2PO_4.2H_2O$ in 250 ml water) of pH 7.3–7.4, and filtered on a 0.2 µm membrane filter (Corning 21052-25). Chitosan solutions were prepared in 14.65 mM phosphate buffer as follows: 2.3 mg/ml CSN LV, 11.5 mg/ml CSN LV, 2.3 mg/ml CSN MV or 11.5 mg/ml CSN MV. Insulin/chitosan formulations were produced by mixing equal volumes of the insulin stock solution and the appropriate chitosan solution, followed by the addition of 0.15 ml of 0.166 M hydrochloric acid for each 1.0 ml of the mixture. The addition of hydrochloric acid proved necessary to ensure that the chitosan remained in solution.

The final formulations thus produced had the following composition:

Formulation 1: 200 IU/ml insulin+0.1% CSN LV, pH 3.6
Formulation 2: 200 IU/ml insulin+0.5% CSN LV, pH 4.4
Formulation 3: 200 IU/ml insulin+0.1% CSN MV, pH 3.6
Formulation 4: 200 IU/ml insulin+0.5% CSN MV, pH 4.4

The sheep were divided into 4 groups, each of 3 animals, with each sheep receiving 2.0 IU/kg insulin intranasally in the form of an aqueous solution of Formulation 1, 2, 3 or 4, corresponding to Groups 1 to 4.

For the intranasal studies, the sheep were sedated by use of an i.v. dose of ketamine hydrochloride at 2.25 mg/kg. This was intended as a counter-measure against the animal sneezing during administration. The anaesthesia lasted for about 3 minutes. Blood samples of 6 ml were collected onto crushed ice from the cannulated jugular vein of the sheep at 15 and 5 min prior to the insulin administration and at various times post-administration. Each blood sample was divided into two parts. For insulin analysis, the blood collected (4.0 ml) was mixed gently in 5 ml heparinised (Li Heparin) tubes. For glucose analysis, the blood collected (2.0 ml) was mixed gently in 5 ml fluoride oxalate tubes. The plasma was separated by centrifugation at 4° C. and 3000 rpm, and then stored at –20° C. awaiting insulin and glucose analysis.

The following results were obtained:

TABLE 2

| | Mean blood glucose level (mmol/l) | |
| --- | --- | --- |
| | 5 mins post-administration | 75 mins post-administration |
| Group 1 | 3.4 | 3.0 |
| Group 2 | 3.4 | 2.5 |
| Group 3 | 3.4 | 2.6 |
| Group 4 | 3.8 | 1.8 |

I claim:

1. A method of systemically delivering a pharmaceutically effective amount of a pharmacologically active compound to a mammal comprising:

administering to a mucosal surface a composition including a pharmacologically active compound in a pharmaceutically effective amount when administered systemically and a polymeric substance having a plurality of cationic groups having a molecular weight of 10,000 or more providing for absorption of the active compound across the mucosal surface of the mammal for systemic distribution of the active compound, wherein the polymeric substance is selected from the group consisting of polycationic carbohydrates, polyaminoacids, polyquaternary compounds, protamine, polyimines, polymers having a cationic DEAE group, polyvinylpyridine, polymethacrylates, polyacrylates, polyoxethanes, polyamidoamines, polythiodiethylamino methylethylene, and poly-p-aminostyrene, and (i) the substance is not a polyamino acid which chelates calcium or magnesium ions, (ii) the composition does not consist of microcapsules coated with DEAE-dextran, (iii) if for administration to gut mucosa, the composition does not consist of the active compound and a solution of DEAE-dextran, and (iv) if in the form of a tablet for retention in the mouth, the composition does not comprise chitosan, and allowing the composition to remain in contact with mucosa for a time sufficient for a pharmaceutically effective amount of the pharmacologically active compound to pass through the mucosa.

2. The method according to claim 1 wherein the site of administration is selected from the group consisting of nasal mucosa, vaginal mucosa and gut mucosa of said mammal.

3. The method according to claim 1 wherein the polymeric substance comprises microspheres.

4. The method according to claim 1 wherein the polymeric substance comprises a solution.

5. The method according to claim 4 wherein the concentration of the polymeric substance is between about 0.1% and 15% w/v.

6. The method according to claim 1 wherein the polymeric substance comprises a dispersion.

7. The method according to claim 6 wherein the concentration of the polymeric substance is between about 0.1% and 15% w/v.

8. The method according to claim 1 wherein the pharmacologically active compound is selected from the group consisting of insulin, antimicrobial agents, anesthetics, vasoconstrictors, vasodilators, cardiotonics, enzymes, anti-inflammatories, hormones, bone metabolism controlling agents, hypotensives, sedatives, anti-tumor agents, antihistamines, antitussive, vaccines, and antiasthmatic agents.

9. The method according to claim 1 wherein the polymeric substance is selected from the group consisting of DEAE-dextran, DEAE imine, DEAE methacrylate, DEAE acrylamide and chitosans.

10. A method to produce a composition for transmucosal administration and systemic distribution of a pharmaceutically active compound to a mammal comprising:

combining a pharmacologically active compound in an pharmaceutically effective amount for systemic distribution and a polymeric substance having a plurality of cationic groups, wherein the polymeric substance having a molecular weight of 10,000 or more which is suitable for application to mucosa and is selected from the group consisting of polycationic carbohydrates, polyaminoacids, polyquaternary compounds, protamine, polyimines, polymers having a cationic DEAE group, polyvinylpyridine, polymethacrylates, polyacrylates, polyoxethanes, polyamidoamines, polythiodiethylamino methylethylene, and poly-p-aminostyrene, and (i) the substance is not a polyamino acid which chelates calcium or magnesium ions, (ii) the composition does not consist of microcapsules coated with DEAE-dextran, (iii) if for administration to gut mucosa, the composition does not consist of the active compound and a solution of DEAE-dextran, and (iv) if in the form of a tablet for retention in the mouth, the composition does not comprise chitosan.

11. A composition for transmucosal administration for systemic distribution by application to healthy mucosa in a mammal comprising:

a pharmacologically active compound in a pharmaceutically effective amount for systemic distribution; and a polymeric substance having a plurality of cationic groups having a molecular weight of 10,000 or more, wherein the polymeric substance is selected from the group consisting of polyaminoacids, polyquaternary compounds, protamine, polyvinylpridine, polythiodiethylaminomethylethylene, poly-p-aminostyrene, polycationic carbohydrates other than chitosan in a carrier suitable only for topical administration, polyimines, polymers having a cationic DEAE group, polymethacrylates, polyacrylates, polyoxethanes, and polyamidoamines, wherein (i) the polymeric substance is not a polyamino acid which chelates calcium or magnesium ions, (ii) the composition does not consist of microcapsules coated with DEAE-dextran, (iii) if for administration to gut mucosa, the composition does not consist of the active compound and a solution of DEAE-dextran; wherein the polymeric composition is acceptable for administration to mucosa and remains at the site for a sufficient time for passage of the pharmacologically active compound into the system of the mammal.

12. The composition according to claim 11 wherein the polymeric substance comprises microspheres.

13. The composition according to claim 11 wherein the polymeric substance comprises a solution.

14. The composition according to claim 13 wherein the concentration of the polymeric substance is between about 0.1% and 15 % w/v.

15. The composition according to claim 11 wherein the polymeric substance comprises a dispersion.

16. The composition according to claim 15 wherein the concentration of the polymeric substance is about 0.5–15% w/v.

17. The composition according to claim 11 wherein the pharmacologically active compound is selected from the group consisting of insulin, antimicrobial agents, anesthetics, vasoconstrictors, vasodilators, cardiotonics, enzymes, anti-inflammatories, hormones, bone metabolism controlling agents, hypotensives, sedatives, anti-tumor agents, antihistamines, antitussive, vaccines and antiasthmatic agents.

18. The composition according to claim 11 wherein the polymeric substance is selected from the group consisting of DEAE-dextran, DEAE imine, DEAE methacrylate, DEAE acrylamide, polylysine, polyhistidine, and polyvinyl pyrrolidone methylamino methacrylate.

19. The method of claim 1 wherein the active drug is a vaccine.

20. The composition of claim 11 wherein the active drug is a vaccine.

* * * * *